(12) United States Patent
Mori et al.

(10) Patent No.: US 11,141,126 B2
(45) Date of Patent: Oct. 12, 2021

(54) MEDICAL APPARATUS AND METHOD

(71) Applicant: Toshiba Energy Systems & Solutions Corporation, Kawasaki (JP)

(72) Inventors: Shinichiro Mori, Chiba (JP); Koki Yanagawa, Tokorozawa (JP); Ryusuke Hirai, Shinagawa (JP); Shinya Fukushima, Fuchu (JP); Keiko Okaya, Setagaya (JP)

(73) Assignee: Toshiba Energy Systems & Solutions Corporation, Kawasaki (JP)

( * ) Notice: Subject to any disclaimer, the term of this patent is extended or adjusted under 35 U.S.C. 154(b) by 0 days.

(21) Appl. No.: 16/223,608

(22) Filed: Dec. 18, 2018

(65) Prior Publication Data
US 2019/0183447 A1    Jun. 20, 2019

(30) Foreign Application Priority Data
Dec. 20, 2017    (JP) ............... JP2017-244067

(51) Int. Cl.
| | |
|---|---|
| *A61B 6/00* | (2006.01) |
| *G06T 7/70* | (2017.01) |
| *G06T 7/20* | (2017.01) |
| *A61N 5/10* | (2006.01) |
| *A61B 5/00* | (2006.01) |
| *A61B 5/113* | (2006.01) |

(52) U.S. Cl.
CPC ............ *A61B 6/5288* (2013.01); *A61B 6/463* (2013.01); *A61B 6/467* (2013.01); *A61N 5/1037* (2013.01); *G06T 7/20* (2013.01); *G06T 7/70* (2017.01); *A61B 5/0071* (2013.01); *A61B 5/113* (2013.01); *A61N 5/1049* (2013.01); *A61N 5/1068* (2013.01); *A61N 2005/1061* (2013.01); *A61N 2005/1062* (2013.01); *A61N 2005/1074* (2013.01)

(58) Field of Classification Search
CPC ............... A61N 5/1037; A61N 5/1068; A61N 2005/1061; A61N 5/1049; A61N 2005/1062; A61N 2005/1074; A61N 5/103; A61N 5/1067; A61N 2005/1051; A61N 2005/1059; A61B 6/5288; A61B 6/463; A61B 6/467; A61B 5/0071; A61B 5/113; G06T 7/70; G06T 7/20
See application file for complete search history.

(56) References Cited

U.S. PATENT DOCUMENTS

| | | | |
|---|---|---|---|
| 6,937,696 B1 * | 8/2005 | Mostafavi | A61B 5/113 378/65 |
| 8,611,496 B2 | 12/2013 | Terunuma et al. | |

(Continued)

FOREIGN PATENT DOCUMENTS

JP    2017-144000    8/2017

*Primary Examiner* — William A Beutel
(74) *Attorney, Agent, or Firm* — Oblon, McClelland, Maier & Neustadt, L.L.P.

(57) ABSTRACT

A medical apparatus includes an acquirer, an associator, and a display controller. The acquirer acquires information indicating a respiratory waveform of an object and acquires fluoroscopic images of the object captured in time series. The associator associates a tracking value which fluctuates according to a respiratory phase of the object, based on the time-series fluoroscopic images. The display controller causes a display to display the respiratory waveform and a waveform of the tracking value in a comparable form.

15 Claims, 7 Drawing Sheets

(56) References Cited

U.S. PATENT DOCUMENTS

| | | | |
|---|---|---|---|
| 2002/0138512 A1* | 9/2002 | Buresh | G16H 40/63 |
| | | | 715/214 |
| 2010/0166145 A1 | 7/2010 | Umekawa et al. | |
| 2012/0119115 A1* | 5/2012 | Iwata | A61B 5/08 |
| | | | 250/492.3 |
| 2014/0107390 A1* | 4/2014 | Brown | A61N 5/1045 |
| | | | 600/1 |
| 2014/0343401 A1* | 11/2014 | Huber | A61B 5/055 |
| | | | 600/414 |
| 2016/0022375 A1* | 1/2016 | Blake | A61B 5/06 |
| | | | 600/424 |
| 2016/0082284 A1* | 3/2016 | Ooga | A61N 5/1049 |
| | | | 600/1 |
| 2016/0120497 A1* | 5/2016 | Nasir | A61B 6/56 |
| | | | 378/62 |
| 2017/0231586 A1 | 8/2017 | Hirai et al. | |
| 2017/0304649 A1 | 10/2017 | Sumita et al. | |
| 2019/0143146 A1* | 5/2019 | Fujii | A61N 5/1049 |
| | | | 600/1 |

\* cited by examiner

MEDICAL APPARATUS AND METHOD

CROSS-REFERENCE TO RELATED APPLICATION

This application is based upon and claims the benefit of priority from Japanese Patent Application No. 2017-244067 filed on Dec. 20, 2017; the entire content of which is incorporated herein by reference.

BACKGROUND OF THE INVENTION

Field of the Invention

Embodiments described herein relate generally to a medical apparatus and a control method for a medical apparatus.

Description of Related Art

Therapeutic devices which irradiate a patient (object) with a therapeutic beam such as a heavy particle beam or a radiation are known. There are cases in which a lesion of an object, that is, a spot to be irradiated with a therapeutic beam B moves due to respirations, heartbeat, intestinal movements, and the like. As a therapeutic method suitable therefor, a gated irradiation method and a tracking irradiation method are known.

When a lesion which moves due to respirations is irradiated with a therapeutic beam, there is a need to perform irradiation synchronously with respiratory phases of an object. Techniques of respiratory phase synchronization include a technique of ascertaining the respiratory phase (external respiratory synchronization) by utilizing output values of various sensors attached to the body of an object, and a technique of ascertaining the respiratory phase (internal respiratory synchronization) based on a fluoroscopic image of an object. The processing for respiratory phase synchronization is performed by a medical apparatus which outputs a control signal to a therapeutic device. For example, a medical apparatus controls a therapeutic device by performing wired or wireless communication with the therapeutic device.

Examples of therapeutic devices of this kind include a therapeutic device which displays a respiratory waveform such as an external respiratory waveform during a therapy. Incidentally, even if a respiratory waveform is displayed, the relationship between the respiratory waveform and a therapeutic target position such as a position of a tumor is not clear in some cases.

SUMMARY OF THE INVENTION

An object to be achieved by the present invention is to provide a medical apparatus and method which can inform a user whether a respiratory waveform is significantly related to a therapeutic target position, and a control method for a medical apparatus.

A medical apparatus according to an embodiment includes an acquirer, an associater, and a display controller. The acquirer acquires information indicating an external respiratory waveform from a sensor attached to an object and acquires fluoroscopic images of the object captured in time series. The associater associates a tracking value which fluctuates according to a respiratory phase of the object, based on the time-series fluoroscopic images. The display controller causes a display to display the external respiratory waveform and a waveform of the tracking value in a comparable form.

According to the present embodiment, it is possible to provide a medical apparatus and method, which can inform a user whether a respiratory waveform is significantly related to a therapeutic target position.

DETAILED DESCRIPTION OF THE INVENTION

Hereinafter, a medical apparatus and method according to an embodiment will be described with reference to the drawings. In this application, the expression "based on XX" denotes "based on at least XX" and also includes a case based on another element in addition to XX. The expression "based on XX" is not limited to a case of directly adopting XX and also includes a case based on a result realized by performing computation or processing with respect to XX. The term "XX" indicates an arbitrary element (for example, arbitrary information).

<Configuration>

Figure 1:
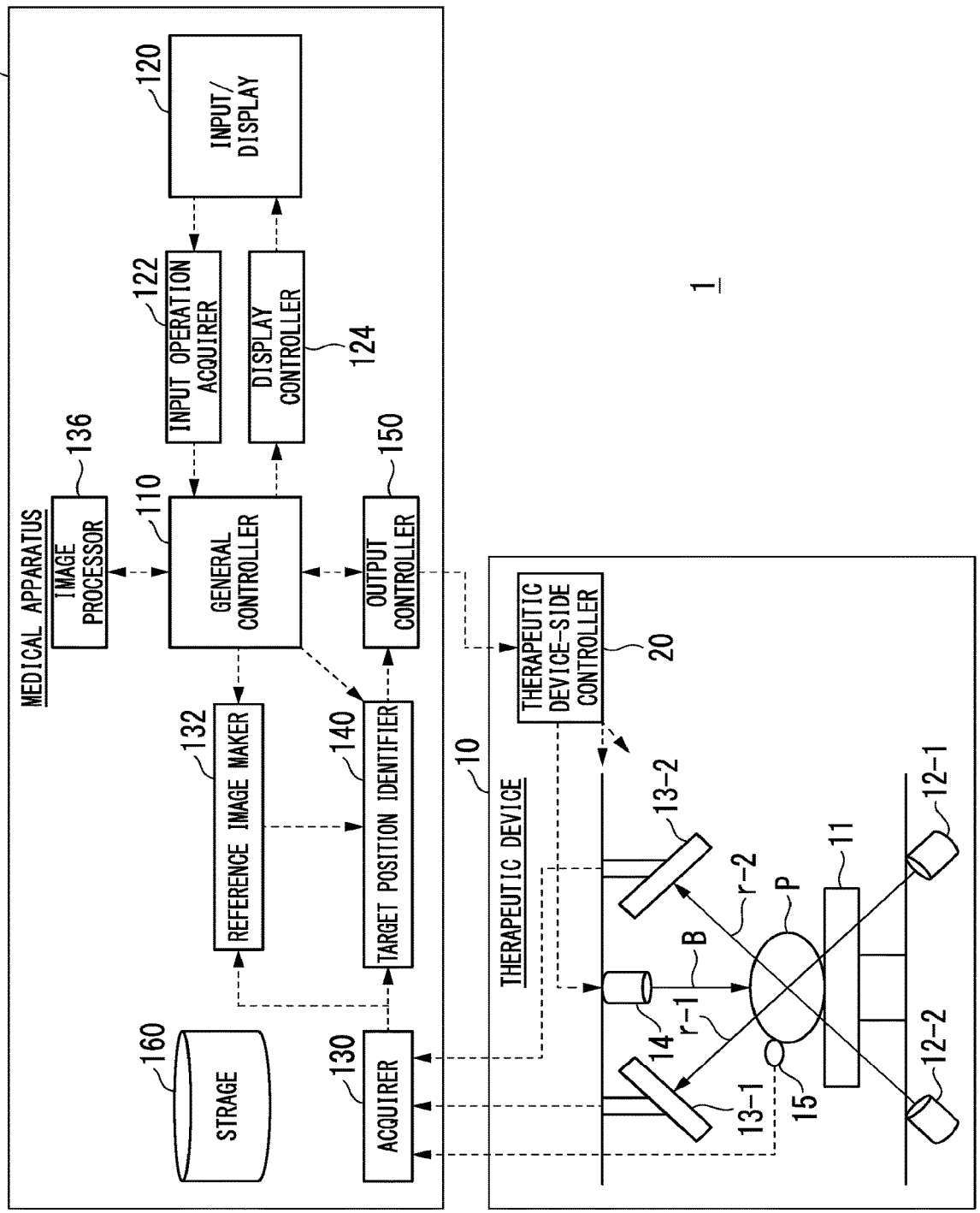
FIG. 1 is a configuration diagram of a therapy system 1 including a medical apparatus.

FIG. 1 is a configuration diagram of a therapy system 1 including a medical apparatus 100. For example, the therapy system 1 includes a therapeutic device 10 and the medical apparatus 100.

For example, the therapeutic device 10 includes a bed 11, radiation sources 12-1 and 12-2, detectors 13-1 and 13-2, an irradiation gate 14, a sensor 15, and a therapeutic device-side controller 20. Hereinafter, a hyphen and a numeral following it in the reference sign indicate a fluoroscopic radiation or a fluoroscopic image realized by a set of a radiation source and a detector. Suitably, the hyphen and the numeral following it in the reference sign may be omitted in description.

An object P to be treated is fixed to the bed 11. The radiation source 12-1 irradiates the object P with a radiation r-1. The radiation source 12-2 irradiates the object P with a radiation r-2 at an angle different from that of the radiation source 12-1. The radiations r-1 and r-2 are examples of electromagnetic waves and are X-rays, for example. Hereinafter, description will be given on this premise.

The radiation r-1 is detected by the detector 13-1, and the radiation r-2 is detected by the detector 13-2. For example, the detectors 13-1 and 13-2 are flat panel detectors (FPD), image intensifiers, or color image intensifiers. The detector 13-1 detects energy of the radiation r-1, performs digital conversion, and outputs the conversion result to the medical apparatus 100 as a fluoroscopic image TI-1. The detector 13-2 detects energy of the radiation r-2, performs digital conversion, and outputs the conversion result to the medical apparatus 100 as a fluoroscopic image TI-2. In FIG. 1, two sets of the radiation source and the detector are illustrated. However, the therapeutic device 10 may include three or more sets of the radiation source and the detector.

In a therapy stage, the irradiation gate 14 irradiates the object P with a therapeutic beam B. Examples of the therapeutic beam B include a heavy particle beam, an X-ray, a γ-ray, an electron beam, a proton beam, and a neutron beam. In FIG. 1, only one irradiation gate 14 is illustrated. However, the therapeutic device 10 may include a plurality of irradiation gates.

The sensor 15 is provided to recognize an external respiratory phase of the object P and is attached to the body of the object P. For example, the sensor 15 is a pressure sensor. The sensor 15 detects a pressure received from the object P, based on a voltage value (detection value). A voltage value detected by the sensor 15 corresponds to the external respiratory phase.

The therapeutic device-side controller 20 operates the radiation sources 12-1 and 12-2, the detectors 13-1 and 13-2, and the irradiation gate 14 in response to a control signal from the medical apparatus 100.

For example, the medical apparatus 100 includes a general controller 110, an input/display 120, an input operation acquirer 122, a display controller 124, an acquirer 130, a reference image maker 132, an image processor 136, a target position identifier 140, an output controller 150, and a storage 160. For example, at least a part of each of the general controller 110, the input operation acquirer 122, the display controller 124, the acquirer 130, the reference image maker 132, the target position identifier 140, and the output controller 150 is realized by a hardware processor such as a central processing unit (CPU) or a graphics processing unit (GPU) executing a program (software) stored in the storage 160. A part or all of these constituent elements may be realized by hardware (circuit section; including circuitry) such as a large scale integration (LSI), an application specific integrated circuit (ASIC), a field-programmable gate array (FPGA), or a graphics processing unit (GPU) or may be realized by cooperation of software and hardware.

Hereinafter, the function of each part of the medical apparatus 100 will be described. In description of the medical apparatus 100, unless otherwise identified, processing performed with respect to the fluoroscopic image TI will be regarded to be executed in parallel with both the fluoroscopic images TI-1 and TI-2. The general controller 110 generally controls the functions of the medical apparatus 100.

For example, the input/display 120 includes a display device such as a liquid crystal display (LCD), an organic electroluminescence (EL) display device, or a light emitting diode (LED) display; and an input device which receives an input operation performed by an operator. The input/d display 120 may be a touch panel in which a display device and an input device are integrally formed or may include an input device such as a mouse and a keyboard.

The input operation acquirer 122 recognizes the details of an operation (touching, flicking, swiping, clicking, dragging, key-inputting, or the like) performed with respect to the input/display 120 and outputs the details of the recognized operation to the general controller 110. The display controller 124 causes the input/display 120 to display an image in response to an instruction from the general controller 110. The display controller 124 causes the input/display 120 to display an interface screen for receiving an instruction to start each of a preparation stage of a therapy and an irradiation stage of the therapeutic beam B. Displaying of an image includes generation of elements of an image performed based on a computation result and allocation of elements of an image made in advance to a display screen.

The acquirer 130 acquires the fluoroscopic image TI from the therapeutic device 10. The acquirer 130 acquires a detection value of the sensor 15. The acquirer 130 acquires three-dimensional volume data of the object P from a medical inspection device (not illustrated). When the fluoroscopic image TI is used as a reference image to identify the position of a target, the reference image maker 132 generates a reference image to be used for identifying a target position, based on the fluoroscopic image TI acquired by the acquirer 130. These will be described below in detail.

The image processor 136 performs image processing such as deformable registration and a digitally reconstructed radiograph (DRR) image generation. Deformable registration is processing performed with respect to time-series three-dimensional volume data, in which positional information designated for three-dimensional volume data at a certain point of time is deployed in three-dimensional volume data at another point of time. A DRR image is a virtual fluoroscopic image generated from three-dimensional volume data to correspond to a radiation when it is assumed that irradiation of this radiation is performed from a virtual radiation source with respect to the three-dimensional volume data.

The target position identifier 140 identifies the position of a target in the fluoroscopic image TI. A target may be a lesion of the object P, that is, a position to be irradiated with the therapeutic beam B, or may be a marker or a characteristic spot of the object P. Since the difference between a characteristic spot such as the diaphragm, the heart, or a bone and surrounding spots appears in a relatively clear manner in the fluoroscopic image TI, the characteristic spot is a spot of which the position can be easily identified when a computer analyzes the fluoroscopic image TI. The target position may be one point or a region having a two-dimensional or three-dimensional spread.

The output controller 150 outputs an irradiation permission signal to the therapeutic device 10 based on the target position identified by the target position identifier 140. For example, in a gated irradiation method, when the target position is settled within a gating window, the output controller 150 outputs a gate-on signal to the therapeutic device 10. A gating window is a region set in a two-dimensional plane or a three-dimensional space and is an example of an irradiation permission range. A gate-on signal is a signal for instructing an operator to irradiate the object P with the therapeutic beam B and is an example of an irradiation permission signal. Hereinafter, description will be given on these premises. The therapeutic device 10 performs irradiation of the therapeutic beam B when a gate-on signal is input, and does not perform irradiation of the therapeutic beam B when no gate-on signal is input. The irradiation permission range is not limited to a fixedly set range and may be a range which moves in a manner following a movement of a lesion.

For example, the storage 160 is realized by a random access memory (RAM), a read only memory (ROM), a hard disk drive (HDD), or a flash memory. The storage 160 stores time-series three-dimensional CT images (hereinafter, 4D CT images), the fluoroscopic image TI, an output value of the sensor 15, and the like, in addition to the program described above.

<Flow of Therapy>

Hereinafter, a flow of a therapy of the therapy system 1 will be described. A therapy of the therapy system 1 is performed in a manner of being divided into a plurality of stages, such as a planning stage, a positioning stage, the preparation stage, and the therapy stage.

Here, the flow of a therapy in each stage will be described. For example, the therapy system 1 can perform a therapy by switching between three modes, such as markerless tracking and marker tracking which are internal respiratory synchronization, and external respiratory synchronization. Here, markerless tracking will be described. Markerless tracking includes a technique of using a template matching method or machine learning. Hereinafter, markerless tracking using the template matching method will be described, and description will be given such that the gated irradiation method is employed as an irradiation method. The medical apparatus 100 may be switchable between the template matching method and a technique using machine learning.

[Planning Stage]

In the planning stage, first, CT image-capturing of the object P is performed. In CT image-capturing, images of the object P are captured in various directions for each of various respiratory phases. Next, 4D CT images are generated based on the results of the CT image-capturing. 4D CT images are n three-dimensional CT images (an example of the three-dimensional volume data described above) arranged in time series. A period obtained by multiplying this number n by the time interval between the time-series images is set to cover a period in which the respiratory phase changes by one cycle, for example. 4D CT images are stored in the storage 160.

Next, a physician, a radiologist, or the like inputs a contour with respect to one CT image of n CT images, for example. This contour is a contour of a tumor (a therapeutic target) which is a lesion or a contour of an organ which is not intended to be irradiated with the therapeutic beam B. Next, for example, the image processor 136 sets the contour for each of n CT images through deformable registration. Next, a therapeutic plan is decided. A therapeutic plan is a plan for regulating irradiation of the place, the direction, and the quantity of the therapeutic beam B in accordance with the position of a lesion based on information of the set contour. The therapeutic plan is decided in accordance with a therapeutic method such as the gated irradiation method or a tracking irradiation method. A part or all of the processing in the planning stage may be executed by an external device. For example, processing of generating 4D CT images may be executed by a CT device.

Here, a region defined by the contour of a tumor, the center of gravity in this region, the position of a characteristic spot of the object P, or the like becomes a target position. Moreover, in the therapeutic plan, the position which may be irradiated with the therapeutic beam B is decided as a target position. When the contour is set through deformable registration, a margin is automatically or manually set for the target position, and a gating window is set by applying the margin. This margin is provided to absorb a positioning error and the like.

[Positioning Stage]

In the positioning stage, the bed position is adjusted. The object P is laid on the bed 11 and is fixed by using a shell or the like. First, the bed position is roughly adjusted. In this stage, a worker visually checks for the position and the posture of the object P and moves the bed 11 to a position at which the object P will be irradiated with the therapeutic beam B from the irradiation gate 14. Accordingly, the position of the bed 11 is roughly adjusted. Next, an image to be utilized for minutely adjusting the bed position is captured. For example, when 3D-2D registration is performed, the fluoroscopic image TI is captured. For example, the fluoroscopic image TI is captured at the timing of the end of exhalation of the object P. Since the position of the bed 11 has already been roughly adjusted, an area near a lesion of the object P is imaged in the fluoroscopic image TI.

When 3D-2D registration is performed, in this stage, a DRR image is generated from three-dimensional volume data by using the radiation sources 12-1 and 12-2, the detectors 13-1 and 13-2, and the therapeutic plan information of the object P. The movement amount of the bed is calculated based on the DRR image and the fluoroscopic image TI, and the bed 11 is moved. The position of the bed 11 is minutely adjusted by repeating capturing the fluoroscopic image TI, calculating the movement amount of the bed, and moving the bed 11.

[Preparation Stage (Part 1)]

When the positioning stage ends, the processing shifts to the preparation stage. First, a DRR image of each phase is made from 4D CT images. The DRR image may be made at any time after the 4D CT images have been captured. In this case, a position, at which the gating window set in the therapeutic plan is projected, is set as the gating window on the DRR image. In the preparation stage, first, the fluoroscopic image TI which becomes a target to be selected as a reference image is captured. When the fluoroscopic image TI is captured, a physician or the like instructs the object P to perform deep respirations a plurality of times (twice or more), for example. While the object P performs deep respirations a plurality of times in accordance with the instruction of a physician or the like, the fluoroscopic image TI is captured such that two respirations of the object P are covered. While the object P performs deep respirations, an external respiratory waveform of the object P is acquired synchronously with the fluoroscopic image TI. The display controller 124 causes the input/display 120 to display the acquired external respiratory waveform. A tracking value based on the respiratory phase of the object P obtained from the external respiratory waveform is associated with the captured fluoroscopic image TI.

In this stage, the relationship between the fluoroscopic image TI and the target position is learned from information of the DRR image and the target position on the DRR image. Moreover, correction of the target position by a physician is received. From the fluoroscopic image TI in which the target position has been learned, one or more reference images are selected based on the tracking value, and a template is generated from the selected reference image. A template may be the fluoroscopic image TI itself which becomes a reference image or may be a cut-out characteristic part of this fluoroscopic image TI. Learning of the target position may be performed at any timing during a period from the planning stage to the therapy stage. For example, when a template is made from the fluoroscopic image TI for one respiration of the first half of the fluoroscopic images TI for two respirations of the object P, whether a target can be tracked with the fluoroscopic image TI for one respiration of the second half may be checked by using the template. In this case, the display controller 124 may cause the gating window set on the DRR image to be displayed on the fluoroscopic image TI. In this case, the display controller 124 causes the input/display 120 to display the external respiratory waveform and a coordinate position for each of the X coordinate, the Y coordinate, and the Z coordinate of the target position in a manner of being associated with the fluoroscopic image TI.

[Preparation Stage (Part 2)]

Capturing the fluoroscopic image TI is restarted. The target position identifier 140 performs matching of the template with respect to the fluoroscopic images TI input in time series and allocates the target position with respect to the fluoroscopic image TI. While causing the input/display 120 to display the fluoroscopic images TI as a moving image, the display controller 124 causes the target position to be displayed in a manner of being superimposed on a frame of the fluoroscopic image TI in which the target position is allocated. As a result, the tracking results of the target position are checked by a physician or the like.

In this case, the display controller 124 causes the gating window set on the DRR image to be displayed on the fluoroscopic image TI. The output controller 150 determines whether or not the target position is settled within the gating window, regarding both the fluoroscopic images TI-1 and TI-2. In the therapy stage, a gate-on signal is output to the therapeutic device 10 when the target position is settled within the gating window. However, in the preparation stage, the presence or absence of an output of a gate-on signal (whether a gate-on signal is output or not) is transmitted to the display controller 124 via the general controller 110. The display controller 124 causes the input/display 120 to display the presence or absence of an output of a gate-on signal in parallel with displaying of the moving image. As a result, the output timing of a gate-on signal is checked by a physician or the like.

[Therapy Stage]

In the therapy stage, the display controller 124 causes the gating window set on the DRR image to be displayed on the fluoroscopic image TI. The output controller 150 outputs a gate-on signal to the therapeutic device 10 when the target position is settled within the gating window, regarding both the fluoroscopic images TI-1 and TI-2. Accordingly, a therapy is performed by means of irradiation of the therapeutic beam B. In the case in which the target position is the position of a lesion, the lesion of the object P is irradiated with the therapeutic beam B when the tracked target position is settled within the gating window. In the case in which the target position is the position of a characteristic spot of the object P, irradiation of the therapeutic beam B is performed when the position of a lesion derived out from the target position is settled within the gating window, based on the relationship between the target position learned in advance and the position of a lesion. A portion at the position of a lesion may be irradiated with the therapeutic beam B by these complex techniques. That is, irradiation of the therapeutic beam B may be performed when a lesion is settled within a first gating window and a characteristic spot is settled within a second gating window, by setting each of the position of a lesion and the position of a characteristic spot as the target position.

<Display Image and Flowchart>

Hereinafter, processing of the medical apparatus 100 for supporting the flow of a therapy described above will be described.

Figure 2:
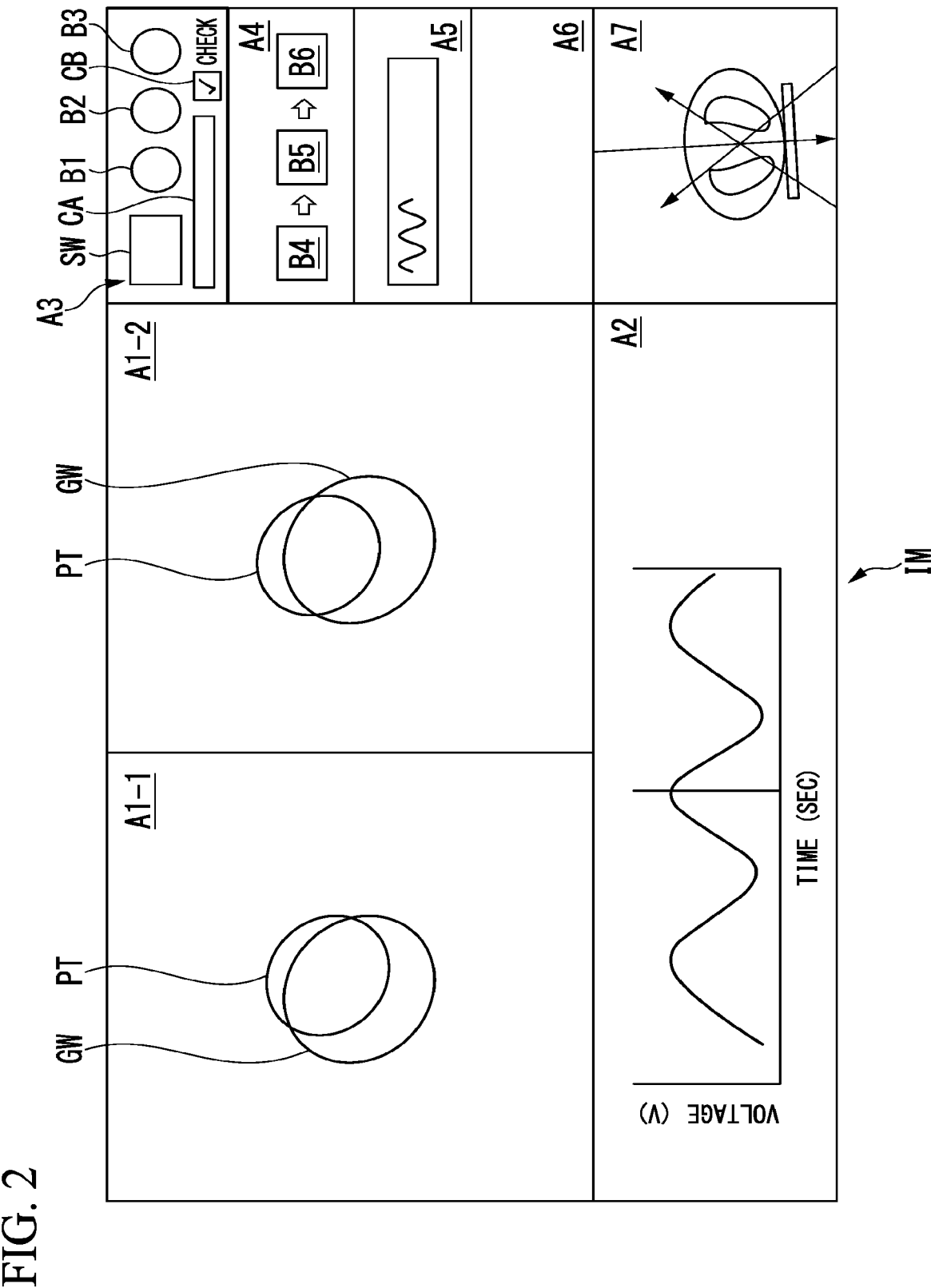
FIG. 2 is a view illustrating an example of an interface image displayed by an input/display of the medical apparatus.

FIG. 2 is a view illustrating an example of an interface image IM which is displayed by the input/display 120 of the medical apparatus 100. For example, the interface image IM includes regions A1-1, A1-2, A2, A3, A4, A5, A6, and A7.

In the region A1-1, a gating window GW or a target position PT is displayed in a manner of being superimposed on the fluoroscopic image TI-1. In the region A1-2, the gating window GW or the target position PT is displayed in a manner of being superimposed on the fluoroscopic image TI-2. In the region A2, various graphs of the external respiratory waveform, the target position, and the like are displayed. In the therapy stage, a state whether or not a gate is on, the presence or absence of an error, a gate-on signal, a gate-on ratio, an error ratio, and the like are also displayed in the region A2, in addition to the graphs. Regarding the state whether or not a gate is on, a gate-on state is indicated when the graph is at a high position, and a non-gate-on state is indicated when the graph is at a low position. Regarding the presence or absence of an error, it is indicated that an error is present when the graph is at a high position and no error is present when the graph is at a low position. An error for the presence or absence of an error includes an error, such as a case in which the moving speed of the tracking value becomes a threshold value or greater due to coughing, sneezing, or the like. Furthermore, examples of an error include the following errors of PED, DBR, PRS, IV, and TAD. A PED error is an error caused by a change in brightness of a calculation region. For example, in PED, it is determined that an error is present when there is a change of 20% in the brightness average. DBR is an error caused by an error of the tracking value of the fluoroscopic image TI-1 displayed in the region A1-1 and the tracking value of the fluoroscopic image TI-2 displayed in the region A1-2. PRS is an error based on the degree of similarity between the template and the fluoroscopic image TI. For example, in PRS, when the diaphragm is not imaged in the template but the diaphragm is imaged in the fluoroscopic image TI, since there is a significant difference between the template and the fluoroscopic image TI in regard to the degree of similarity, it is determined that an error is present. IV is an error based on the speed. In IV, it is determined that an error is present when over-speeding occurs due to sneezing, coughing, or the like. TAD is an error caused when abnormality in the degree of similarity is detected through machine learning. In PRS, it is determined that an error is present based on the numerical value of the degree of similarity. However, in TAD, it is determined that an error is present in the degree of similarity through machine learning. A gate-on signal indicates a signal for allowing irradiation based on the external respiratory waveform or the target position. For example, a gate-on ratio indicates a ratio at which a gate-on signal is output with respect to the therapy time.

For example, an error ratio indicates a ratio of an error signal output time to the therapy time.

In the region A3, a selection window SW for receiving selection of a mode and the like, a first button B1 for instructing the therapeutic device 10 to start capturing or stop capturing the fluoroscopic image TI, a second button B2 for instructing the therapeutic device 10 to temporarily stop capturing the fluoroscopic image TI, a third button B3 for instructing the therapeutic device 10 to end a therapeutic session, a slide bar for tracing back and checking for DRR images or the fluoroscopic images TI in time series, a control area CA in which a frame advancing switch and the like are set, a check box CB for checking for completion of the preparation stage, and the like are set. For example, an operation with respect to each part of the interface image IM is performed by performing a touching operation, clicking a mouse, operating a keyboard, or the like. For example, the first button B1 is operated by performing a touching operation or clicking a mouse.

In the region A4, a fourth button B4, a fifth button B5, and a sixth button B6 for instructing the therapeutic device 10 that the therapy stage corresponding to the mode proceeds to a next step are set. In the region A5, the graph of the external respiratory waveform based on the output value of the sensor 15, and the like are displayed. In the region A6, an image indicating the therapeutic plan information of the object P, and text information are displayed. In the region A7, the irradiation direction of an X-ray, the irradiation field, the irradiation direction of the therapeutic beam B, the contour of a target, the marker ROI, and the like are displayed in a manner of being superimposed on a cross section of a CT image of the object P.

Figure 3:
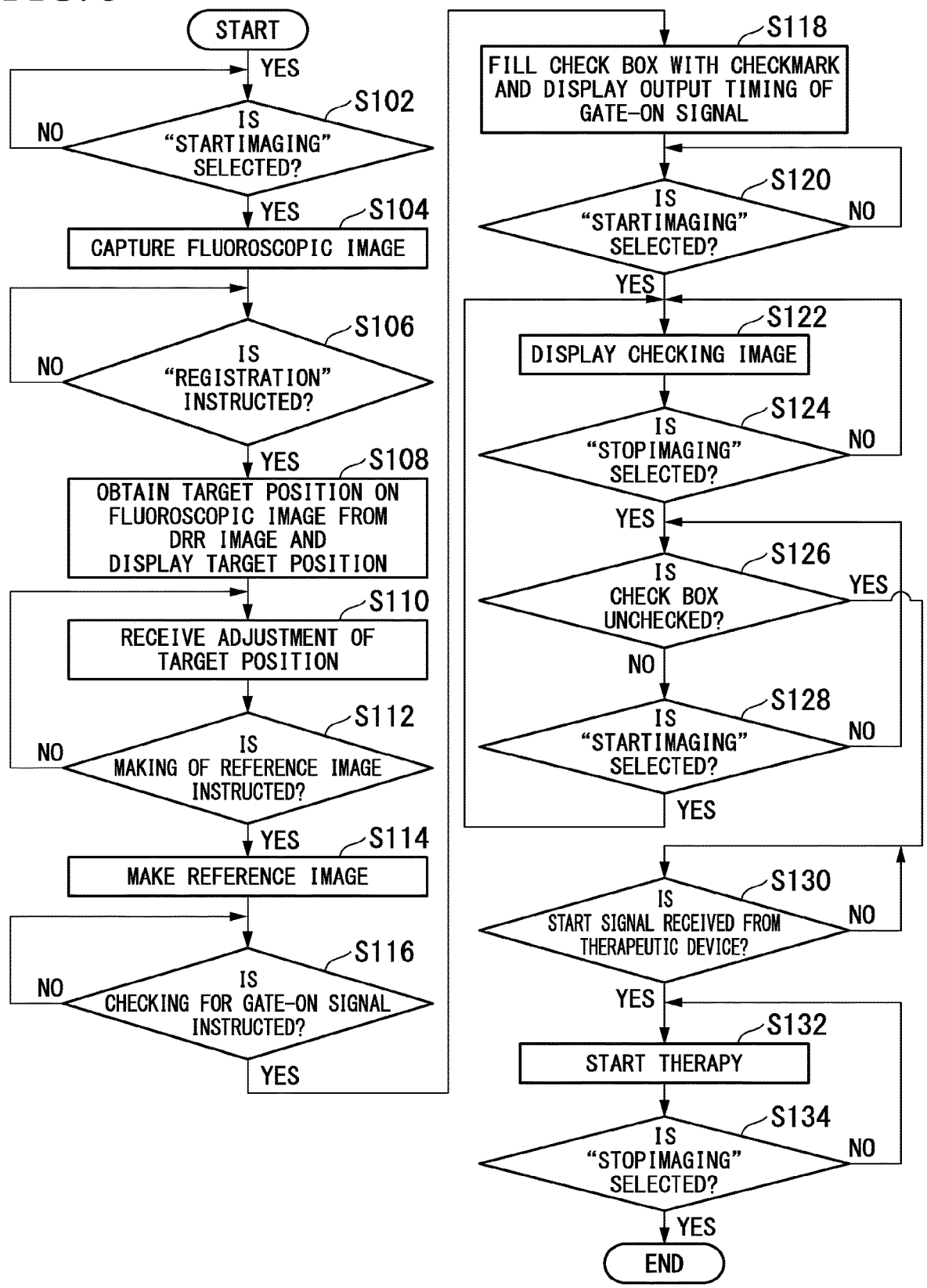
FIG. 3 is a view illustrating an example of a flowchart of a flow of processing executed by the medical apparatus.

Hereinafter, various functions of the interface image IM will be described with reference to the flowchart. FIG. 3 is a flowchart (Part 1) illustrating an example of a flow of processing executed by the medical apparatus 100. In the following description, when it is detected that an operation has been performed with respect to the medical apparatus 100, the general controller 110 is regarded to perform determination with reference to information input from the input operation acquirer 122, and description for each case will be omitted.

Figure 4:
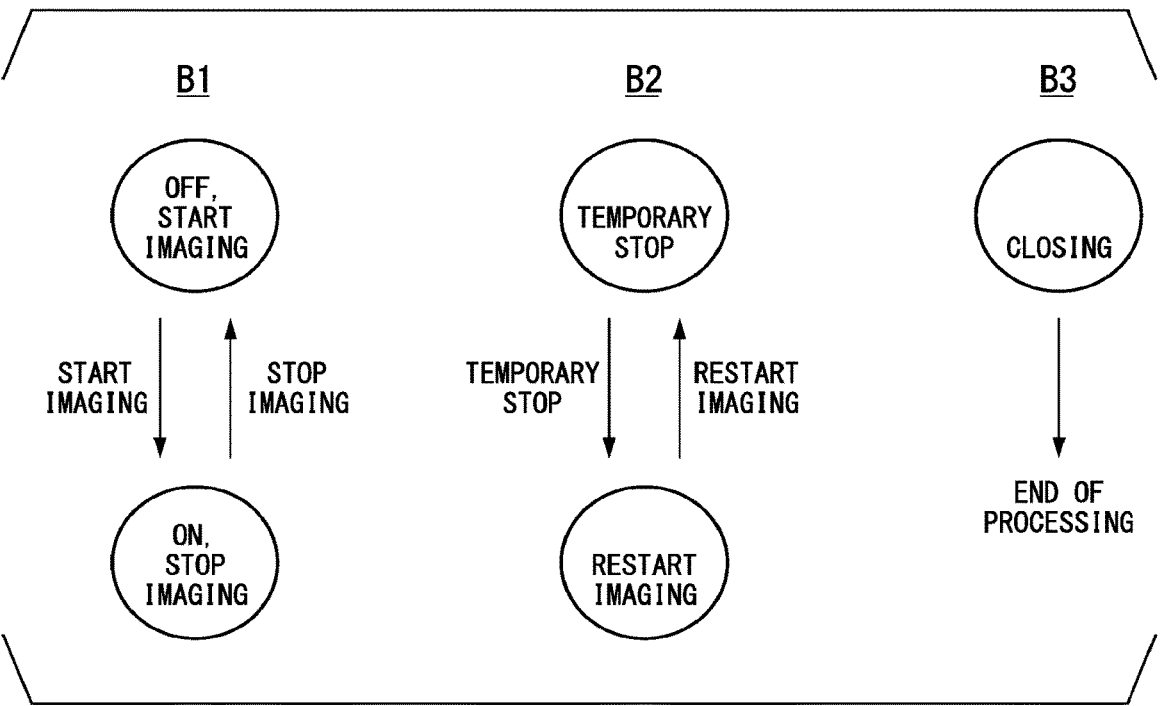
FIG. 4 is a view illustrating a change in a form of displaying a first button, a second button, and a third button.

First, with reference to the information input from the input operation acquirer 122, the general controller 110 determines whether or not start image-capturing is selected by operating the first button B1 (Step S102). FIG. 4 is a view illustrating a change in a form of displaying the first button B1, the second button B2, and the third button B3. As illustrated in the diagram, in an initial state, the first button B1 indicates a state in which image-capturing is "OFF", that is, stopped in a form of receiving an instruction of "start image-capturing". When the first button B1 is operated, a state in which image-capturing is "ON", that is, executed is indicated, and the first button B1 changes into a form of receiving an instruction of "stop image-capturing". The first button B1 performs state transition between these two forms.

In an initial state, the second button B2 is in a form of receiving an instruction of "temporary stop" of image-capturing when being operated. When being operated, the second button B2 changes into a form of receiving an instruction of "restart image-capturing". In an initial state, the third button B3 is in a form of receiving an instruction of "closing" of the interface image IM. When the third button B3 is operated, the interface image IM is stopped being displayed, and a series of processing ends.

When start image-capturing is selected by operating the first button B1, the general controller 110 instructs the output controller 150 to instruct the therapeutic device 10 to capture the fluoroscopic image TI which becomes a template (Step S104). For example, the output controller 150 instructs the therapeutic device 10 to capture the fluoroscopic images TI fork times of respirations.

Figure 5:
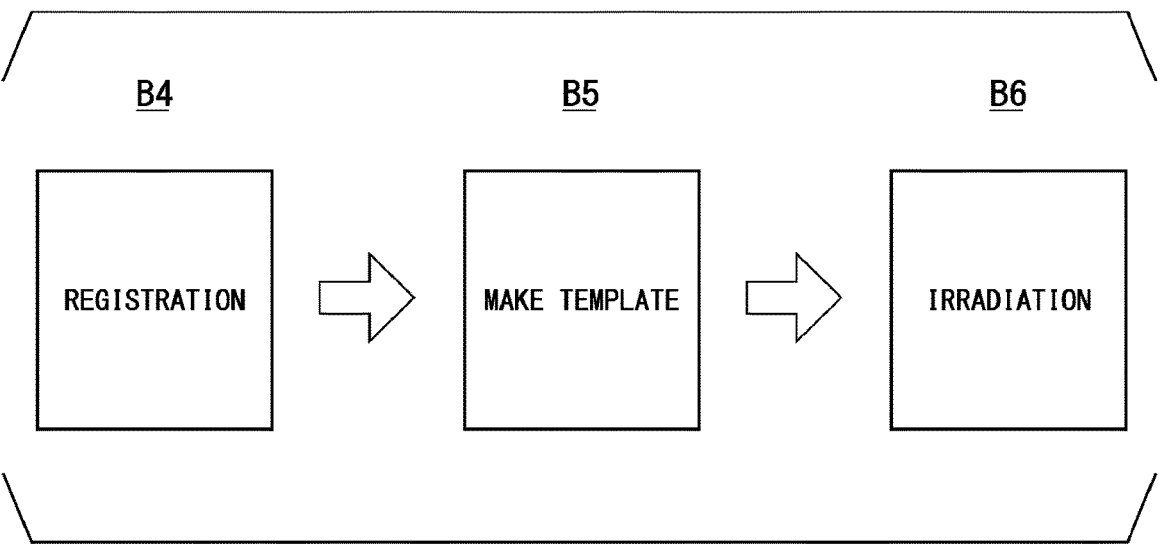
FIG. 5 is a view illustrating details of a fourth button, a fifth button, and a sixth button.

Next, the general controller 110 determines whether or not registration is instructed by operating the fourth button B4 (Step S106). FIG. 5 is a view illustrating details of the fourth button B4, the fifth button B5, and the sixth button B6. The fourth button B4 receives an instruction of registration (learning of the target position PT in the fluoroscopic image TI), the fifth button B5 receives an instruction of selecting a reference image, and the sixth button B6 receives an instruction of checking for a gate-on signal.

When registration is instructed by operating the fourth button B4, the general controller 110 instructs the image processor 136 to obtain a target position in the fluoroscopic image TI from the target position PT in a DRR image, and instructs the display controller 124 to cause the input/display 120 to display the obtained target position PT in a manner of being superimposed on the fluoroscopic image TI (Step S108). As described above, the image processor 136 performs processing of matching characteristic portions in images between the DRR image of which the target position PT is already known and the fluoroscopic image TI, based on the DRR image made from a CT image captured in the planning stage, or the fluoroscopic image TI captured after the planning stage, thereby deriving out the target position PT in the fluoroscopic image TI. The relationship between the fluoroscopic image TI and the target position PT is provided for the reference image maker 132. An image in which the target position PT is superimposed on the fluoroscopic image TI is displayed in the regions A1-1 and A1-2 of the interface image IM, for example.

Figure 6A:
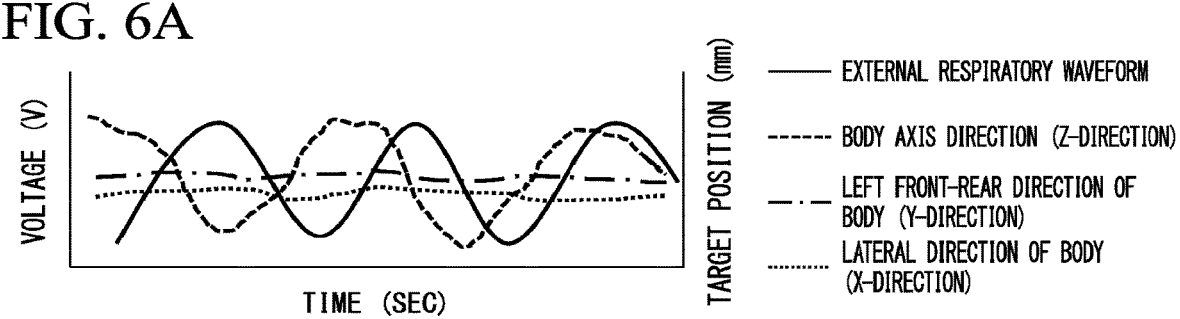
FIG. 6 is a view illustrating a display example of a region of the interface image.

In this case, in the region A2 of the interface image IM, as illustrated in FIG. 6A, the external respiratory waveform and the waveform of the coordinate position of the target position are displayed in a superimposed manner. The coordinate position of the target position is displayed for each of the X coordinate, the Y coordinate, and the Z coordinate. The display controller 124 causes the input/display 120 to display the external respiratory waveform and the waveform of the coordinate position of the target position in a comparable form by displaying the external respiratory waveform and the waveform of the coordinate position of the target position in a superimposed manner. Since the external respiratory waveform and the waveform of the coordinate position of the target position are displayed in a comparable form, when a template is made, it is possible to inform a user whether the external respiratory waveform is significantly related to the target position. As the coordinate position of the target position, only the coordinates having a large movement may be displayed.

In this state, the general controller 110 receives an adjustment of the target position (Step S110). For example, the target position PT is adjusted by performing a drag/drop operation with respect to the regions A1-1 and A1-2. When the target position PT is adjusted, the general controller 110 provides the adjusted relationship between the fluoroscopic image TI and the target position PT for the reference image maker 132.

Next, the general controller 110 determines whether or not selecting a reference image is instructed by operating the fifth button B5 (Step S112). When the fifth button B5 is operated, the general controller 110 instructs the reference image maker 132 to select the fluoroscopic image TI to be used as a reference image and to perform processing such as resizing, thereby making a reference image (Step S114). The reference image maker 132 makes a reference image (template) with which the target position PT is associated and causes the storage 160 to store the reference image.

Next, the general controller 110 determines whether or not checking for a gate-on signal is instructed by operating the sixth button B6 (Step S116). When checking for a gate-on signal is instructed, the general controller 110 instructs the display controller 124 to change the check box CB into a state filled with "✓" (check) and causes the input/display 120 to display the output timing of a gate-on signal (Step S118). In the state in which the check box CB is filled with "✓", the output timing of a gate-on signal is calculated and displayed, but a gate-on signal is not actually output to the therapeutic device 10.

Figure 6B:
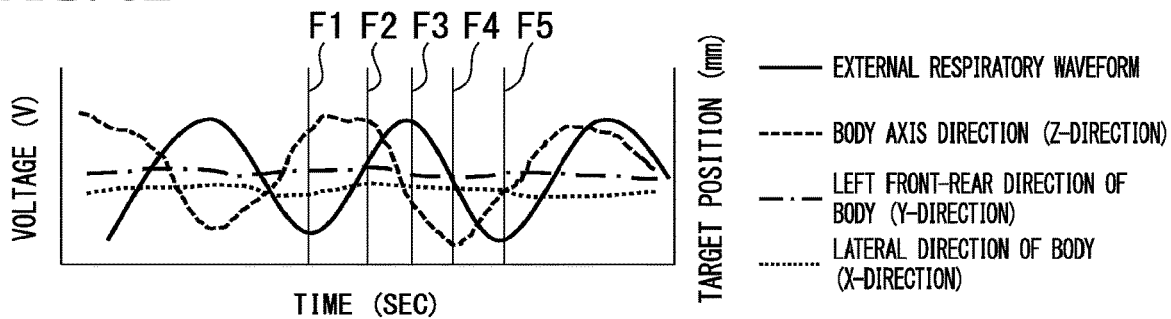

After a template is made, when the fluoroscopic image TI is displayed in the regions A1-1 and A1-2 of the input/display 120 as a moving image, in the region A2, as illustrated in FIG. 6B, the display controller 124 causes image-capturing positions F1, F2, and so on to F5, at which the target image made into a template is captured, to be displayed in the external respiratory waveform and the target position together with positional coordinates. In this manner, it is possible to assist a physician or the like checking for the tracking results of the target position.

Figure 6C:
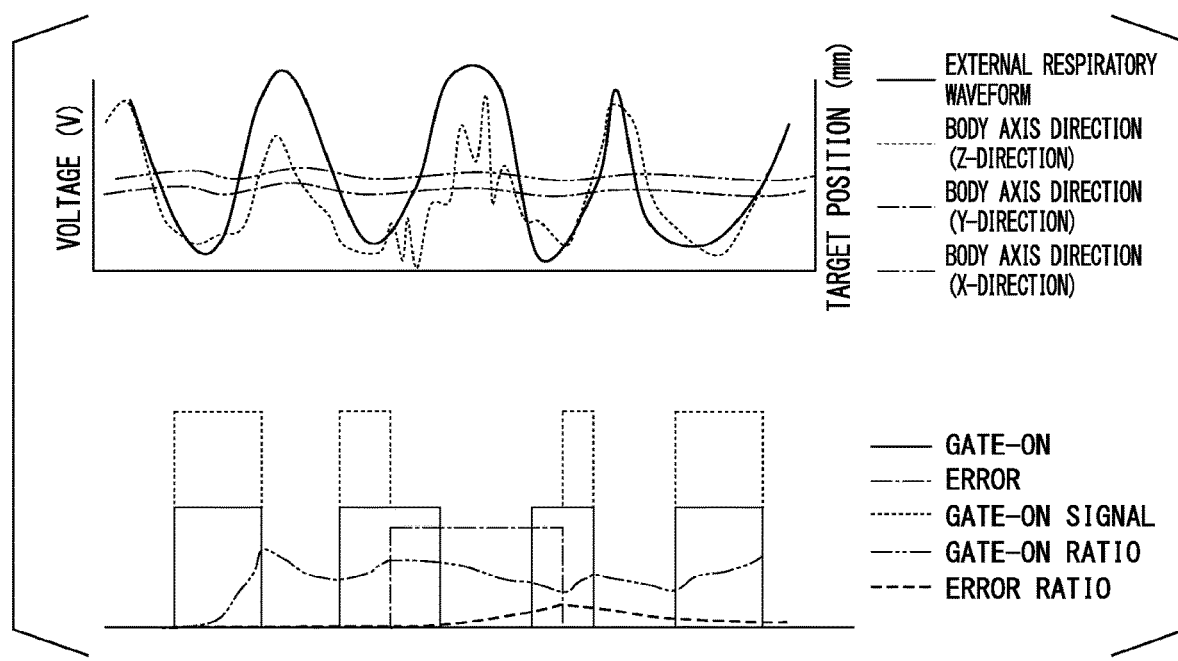

Next, the general controller 110 determines whether or not start image-capturing is selected by operating the first button B1 (Step S120). When start image-capturing is selected by operating the first button B1, the general controller 110 instructs the output controller 150 to instruct the therapeutic device 10 to capture the fluoroscopic image TI and instructs the display controller 124 to cause the input/display 120 to display a checking image using the captured fluoroscopic image TI (Step S122). In the region A2 of the input/display 120, as illustrated in FIG. 6C, the state whether or not a gate is on, the presence or absence of an error, the gate-on signal, the gate-on ratio, the error ratio, and the like are displayed, in parallel with the external respiratory waveform and the target coordinate position. Regarding a gate-on signal, when the target position PT is settled in the gating window GW, a gate signal which has been actually output to the therapeutic device 10 may be displayed. For example, a gate signal which has been output to the therapeutic device 10 is output when the target position PT is settled in the gating window GW and an error signal is not output.

The checking image is displayed in the regions A1-1 and A1-2. The checking image is an image in which the target position PT or the gating window GW is superimposed on the fluoroscopic image TI which is reproduced as a moving image (refer to FIG. 2). The output controller 150 outputs a gate-on signal to the display controller 124, which displays the gate-on signal in the region A2 when the target position PT is settled in the gating window GW. A physician or the like can check for whether or not the target position PT such as a lesion of the object P is recognized as a correct position, whether or not the timing the target position PT is settled in the gating window GW is appropriate, the output efficiency of a gate-on signal, and the like, by visually recognizing this checking image. The checking image is displayed until stop image-capturing is selected by operating the first button B1 (Step S124). Even after stop image-capturing is selected, the checking image can be traced back and checked for by operating the control area CA in which the slide bar, the frame advancing switch, and the like are set.

When stop image-capturing is selected by operating the first button B1, the general controller 110 determines whether or not "✓" of the check box CB is canceled (Step S126). When "✓" of the check box CB is not canceled, the general controller 110 determines whether or not start image-capturing is selected by operating the first button B1 (Step S128). When start image-capturing is selected, the processing returns to Step S122, and when start image-capturing is not selected, the processing returns to Step S126. When "✓" of the check box CB is canceled, the general controller 110 determines whether or not a start signal is received from the therapeutic device 10 (Step S130). This start signal is a signal output when the therapeutic device 10 can start a therapy by operating a switch (not illustrated) of the therapeutic device 10. When a start signal is received from the therapeutic device 10, the general controller 110 instructs the display controller 124, the target position identifier 140, and the output controller 150 to start a therapy, and the output controller 150 instructs the therapeutic device to capture the fluoroscopic image TI (Step S132). When the check box is unchecked in Step S126, even if no start signal is received from the therapeutic device 10, the general controller 110 may determine whether start image-capturing is instructed by operating the first button B1. When the target position PT identified by the target position identifier 140 is settled in the gating window, a gate-on signal may be output to the therapeutic device 10 (not illustrated). In this case, the beam B is not output from the therapeutic device 10. When the check box has not been unchecked in Step S126 but the check box is unchecked after start image-capturing is selected, a gate-on signal may be output in the middle of image-capturing (not illustrated). The target position identifier 140 performs matching of the fluoroscopic image TI and the template, thereby identifying the target position PT. The output controller 150 causes a gate-on signal to be output to the therapeutic device 10 when the target position is settled in the gating window. The display controller 124 causes the input/display 120 to display a therapeutic image in which the target position or the gating window GW is superimposed on the fluoroscopic image TI. The therapeutic image is displayed in the regions A1-1 and A1-2. A therapy continues until stop image-capturing is selected by operating the first button B1 (Step S134). The medical apparatus 100 may end a therapy even when a signal of completing irradiation is received from the therapeutic device 10 or when a signal indicating that an operation of ending irradiation is conducted in the therapeutic device 10 is received from the therapeutic device 10.

The display controller 124 may change the color of the gating window when a gate-on signal is output (in the checking stage, when the conditions for outputting a gate-on signal are fulfilled) in the checking image and the therapeutic image. For example, regarding both the fluoroscopic images TI-1 and TI-2, the border line of the gating window GW may be displayed in a first color when the target position PT is not settled in the gating window GW, may be displayed in a second color when the target position PT is settled in the gating window GW in only one of both the fluoroscopic images TI-1 and TI-2, and may be displayed in a third color when the target position PT is settled in the gating window GW (that is, when the conditions for outputting a gate-on signal are fulfilled) in both the fluoroscopic images TI-1 and TI-2. An error icon may be displayed when the target position PT is not settled in the gating window GW in both the fluoroscopic images TI-1 and TI-2.

When the conditions for outputting a gate-on signal are fulfilled, the display controller 124 may change the hue or the brightness of any of an inner region and an outer region of the gating window GW. Moreover, the medical apparatus 100 may include a notifier that issues notification by a sound or a vibration when the conditions for outputting a gate-on signal are fulfilled.

The mode switching between markerless tracking, marker tracking, and external respiratory synchronization may be received at a suitable timing. For example, the mode switching may be received at an arbitrary timing over a period from the preparation stage to the therapy stage, instead of being received in the processing prior to Step S102 in the flowchart. Suitably, redoing of the processing is received. For example, in a scene displaying the checking image, an operation for redoing the processing from the step of image-capturing a reference image is received. When the mode switching is performed after the fluoroscopic image TI is captured, the fluoroscopic image TI which has already been captured may be employed as a template.

Figure 7:
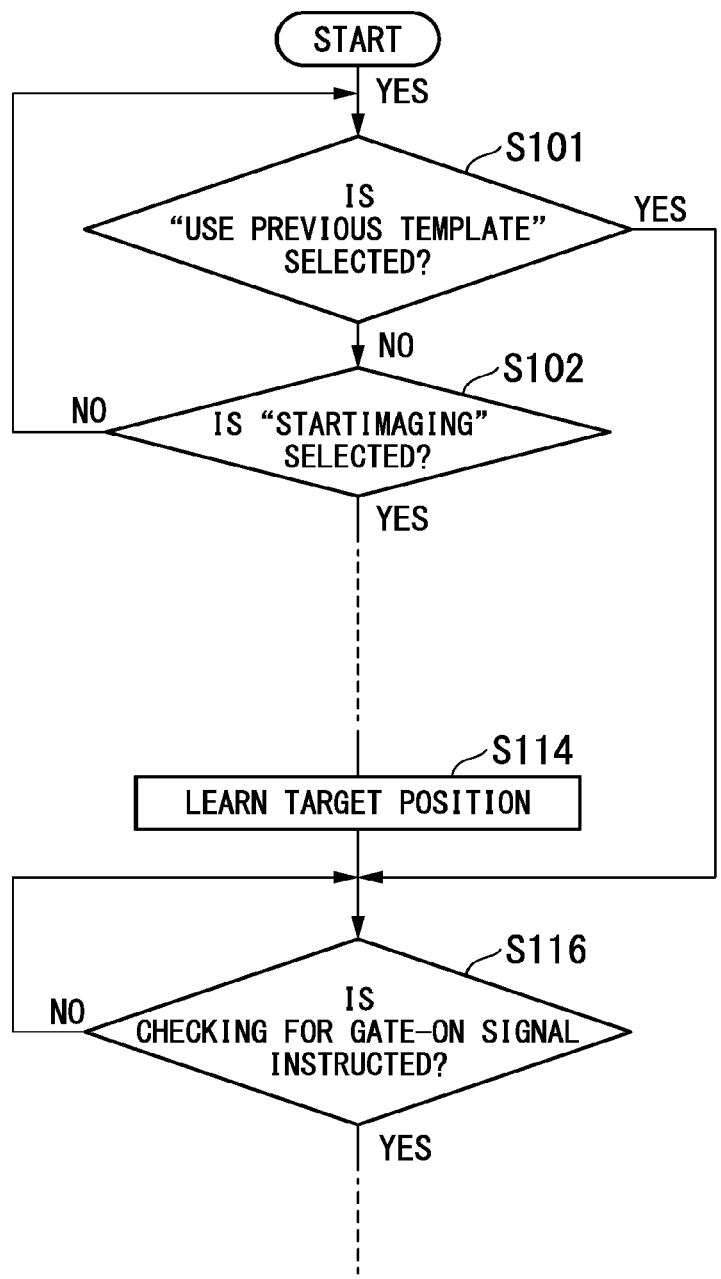
FIG. 7 is a view illustrating an example of another flowchart of a flow of processing executed by the medical apparatus.

When a therapy is performed in a divided manner over a plurality of times, the therapy may be performed by succeeding a template made before a previous therapy. FIG. 7 is a flowchart (Part 2) illustrating an example of a flow of processing executed by the medical apparatus 100. As illustrated in the diagram, after markerless tracking is selected in the selection window SW, the general controller 110 determines whether or not "use previous template" is selected in any of the regions (Step S101). When "use previous template" is selected, the processing skips Steps S102 to S114, and the processing proceeds to Step S116.

The medical apparatus 100 according to the embodiment described above includes the acquirer 130 that acquires information indicating the external respiratory waveform from the sensor 15 attached to the object P and acquires 4D CT fluoroscopic images of the object P captured in time series; an associater 133 that associates the target position which fluctuates according to the respiratory phase of the object P, based on the time-series 4D CT fluoroscopic images; and the display controller 124 that causes the input/display 120 to display the external respiratory waveform and the waveform of the target position in a comparable form. Thus, it is possible to inform a user whether the external respiratory waveform is significantly related to the therapeutic timing.

According to the medical apparatus 100 of the embodiment, the target position is a part or all of the X coordinate, the Y coordinate, and the Z coordinate of an identified position of the object obtained from 4D CT fluoroscopic images. Thus, it is possible to enhance the convenience of determining the relationship between the external respiratory waveform and the therapeutic timing.

The medical apparatus 100 according to the embodiment further includes the target position identifier 140 that identifies the position of a lesion of the object P, and the output controller 150 that outputs a gate-on signal to the therapeutic device 10 which irradiates the object P with a therapeutic beam when the target position identified by the target position identifier 140 is settled within the gating window. The display controller 124 causes the input/display 120 to display the presence or absence of an output of a gate-on signal together with the external respiratory waveform and the waveform of the target position. Thus, it is possible to perform a therapy while checking the relationship between the state of an object and the therapeutic timing.

According to the medical apparatus 100 of the embodiment, the display controller 124 causes the input/display 120 to further display the gate-on ratio. Thus, it is possible to contribute to an accurate therapy.

According to the medical apparatus 100 of the embodiment, the display controller 124 causes the input/display 120 to further display the error ratio. Thus, it is possible to contribute to an accurate therapy.

According to the medical apparatus 100 of the embodiment, the display controller 124 causes the gating window to be displayed in a manner of being superimposed on the fluoroscopic image and changes the color of the gating window when a gate-on signal is output. Thus, it is possible to plainly inform a physician or the like that a gate-on signal is output.

According to the medical apparatus 100 of the embodiment, the display controller 124 causes the gating window to be displayed in a manner of being superimposed on the fluoroscopic image and changes the hue or the brightness of any of the inner region and the outer region of the gating window when a gate-on signal is output. Thus, it is possible to plainly inform a physician or the like that a gate-on signal is output.

The medical apparatus 100 according to the embodiment further includes a notifier that issues notification by a sound or a vibration when a gate-on signal is output. Thus, it is possible to plainly inform a physician or the like that a gate-on signal is output.

MODIFICATION EXAMPLE

In each of the steps in the flowchart described in the foregoing embodiment as an example, unless it is against its nature, the execution order may be changed, a plurality of steps may be performed at the same time, or the steps may be performed in a different order every time the steps are performed.

In the foregoing embodiment, the therapeutic device 10 and the medical apparatus 100 are described as separate devices. However, the therapeutic device 10 and the medical apparatus 100 may be an integrated device. When the therapeutic device 10 and the medical apparatus 100 are separate devices, the output controller 150 may be a function built inside the medical apparatus 100.

Figure 8:
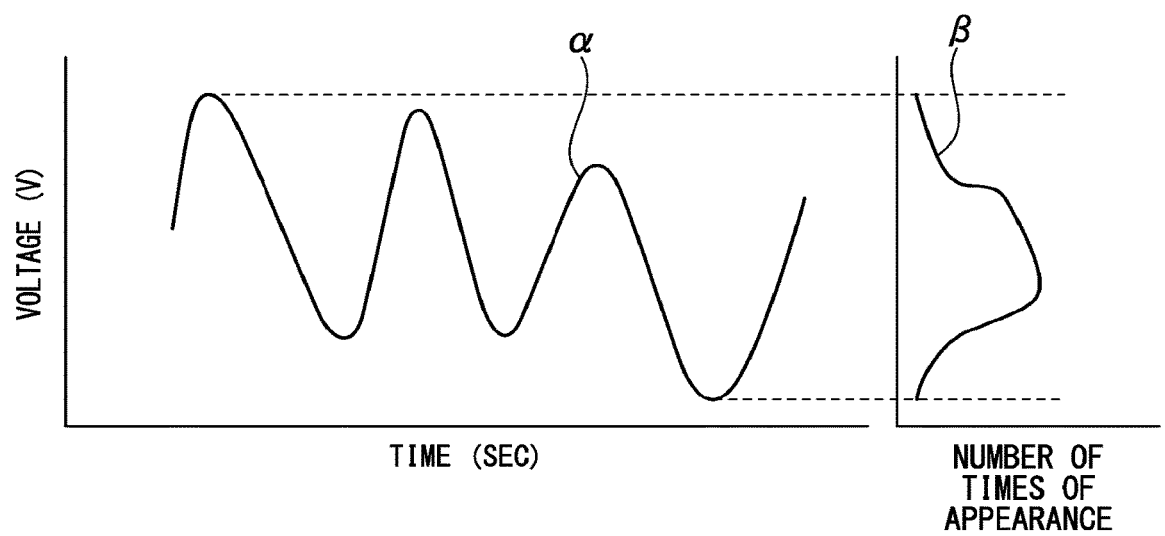
FIG. 8 is a view illustrating an example displaying a waveform of a target position and a histogram.

In the foregoing embodiment, the coordinate position of the target position is expressed in a waveform. However, a histogram of the coordinates of the target position may be made from the waveform expressing the coordinate position of the target position, and may be displayed in the region A2 of the interface image IM. For example, as illustrated in FIG. 8, when the coordinate position of the target position changes in a manner of a waveform a of the target position, a histogram $\beta$ can be made. The histogram $\beta$ is a graph in which a voltage value (respiratory phase) is expressed in the vertical axis and the number of times of appearance is expressed in the horizontal axis. In the external respiratory waveform, since fine vertical movements are included between the maximum exhalation position and the maximum inhalation position, a fluctuation is observed in the number of times of appearance of the voltage value (respiratory phase). For example, when a histogram is made, it can be a target of determining whether irradiation of the object P can be continued. Therefore, for example, when the value of the histogram increases beyond a predetermined threshold value, or when a change in the histogram increases beyond a predetermined threshold value, a warning may be notified. In the foregoing embodiment, the external respiratory waveform and the coordinate position for each of the X coordinate, the Y coordinate, and the Z coordinate of the target position is associated with the fluoroscopic image TI by the display controller 124. However, the external respiratory waveform and the coordinate position for each of the X coordinate, the Y coordinate, and the Z coordinate of the target position may be associated with the fluoroscopic image TI, by providing an associator or the like other than the display controller 124.

According to the medical apparatus of this modification example, the display controller 124 causes the input/display 120 to further display the histogram of the target position. Thus, it is possible to provide a basis of determining whether or not to continue a therapy.

Displaying in which the respiration state of the object P is plainly shown may be performed. For example, a human-like icon having a shape of a human being may be displayed, such that a position corresponding to the abdomen is displayed to be depressed during exhalation and the position corresponding to the abdomen is displayed to swell during inhalation. A physician or the like can easily recognize the respiration state of the object P by performing such displaying.

In the foregoing embodiment, as a respiratory waveform, an external respiratory waveform based on a detection value acquired by the sensor 15 is displayed. However, a different respiratory waveform may be displayed. For example, an image of the body surface may be captured by using a video camera, and the movements due to respirations in the captured video image may be formed into waves and may be displayed as the external respiratory waveform.

The control method for a medical apparatus described in the foregoing embodiment is a control method for a medical apparatus, in which a computer acquires information indicating the respiratory waveform of the object and acquires the fluoroscopic images of the object captured in time series; associates the tracking value which fluctuates according to the respiratory phase of the object, based on the time-series fluoroscopic images; and causes the display to display the respiratory waveform and the waveform of the tracking value in a comparable form.

The program described in the foregoing embodiment is a program which causes a computer to acquire information indicating the respiratory waveform of the object and to acquire the fluoroscopic images of the object captured in time series; to associate the tracking value which fluctuates according to the respiratory phase of the object, based on the time-series fluoroscopic images; and to cause the display to display the respiratory waveform and the waveform of the tracking value in a comparable form.

According to the embodiment described above, a medical apparatus includes an acquirer (130) that acquires information indicating a respiratory waveform of an object (P) and acquires fluoroscopic images (4D CT images) of the object captured in time series; an associator (display controller 124) that associates a tracking value which fluctuates according to a respiratory phase of the object, based on the time-series fluoroscopic images; and the display controller (124) that causes a display (120) to display the respiratory waveform and a waveform of the tracking value in a comparable form. Thus, it is possible to inform a user whether the external respiratory waveform is significantly related to the therapeutic timing.

The foregoing embodiment can be expressed as follows.

A medical apparatus is configured to include a hardware processor and a storage device that stores a program.

The hardware processor executes the program to acquire information indicating a respiratory waveform of an object and to acquire fluoroscopic images of the object captured in time series; to associates the tracking value which fluctuates according to the respiratory phase of the object, based on the time-series fluoroscopic images; and to cause a display to display the respiratory waveform and a waveform of the tracking value in a comparable form.

The embodiment of the present invention has been described. However, the embodiment is presented merely as an example and is not intended to limit the scope of the invention. The embodiment can be performed in various other forms, and various omissions, replacements, and changes can be performed within a range not departing from the gist of the invention. The embodiment and a modification thereof are included in the invention disclosed in Claims and a range equivalent thereto in a manner similar to being included in the scope and the gist of the invention.

What is claimed is:

1. A medical apparatus, comprising:
    circuitry configured to
        acquire information indicating a respiratory waveform of an object and acquire fluoroscopic images of the object captured in time series,
        determine a waveform of a tracking value of a coordinate position of a target position, the waveform of the tracking value being determined independently of the information indicating the respiratory waveform of the object, based directly on the time-series fluoroscopic images, the target position being an identified position of the object;
        determine a waveform of an irradiation permission signal indicating whether the irradiation permission signal is output or not to a therapeutic device having a radiation source that irradiates the object with a therapeutic beam, the waveform of the irradiation permission being determined independently of the information indicating the respiratory waveform of the object, based directly on the time-series fluoroscopic images,
        cause a display to display the respiratory waveform and the determined waveform of the tracking value of the coordinate position of the target position in a comparable form, the respiratory waveform and the determined waveform of the tracking value being displayed in a superimposed manner, and
        cause the display to display, together with the respiratory waveform and the determined waveform of the tracking value, the waveform of the irradiation permission signal, wherein a time axis of the waveform of the irradiation permission signal is aligned with a time axis of the respiratory waveform and the determined waveform of the tracking value.

2. The medical apparatus according to claim 1, wherein the displayed waveform of the tracking value is a part or all of components of coordinates of the target position of an identified position of the object obtained from the fluoroscopic image.

3. The medical apparatus according to claim 1, wherein the circuitry is further configured to
    identify the target position of a position of a tracking target spot of the object,
    output the irradiation permission signal to the therapeutic device based on the identified target position of the tracking target spot, and
    cause the display to display an indication of whether the irradiation permission signal is output or not, together with the respiratory waveform or the waveform of the tracking value.

4. The medical apparatus according to claim 3, wherein the circuitry is further configured to cause the display to display a gate-on ratio.

5. The medical apparatus according to claim 3, wherein the circuitry is further configured to cause the display to display an error ratio.

6. The medical apparatus according to claim 3, wherein the circuitry is further configured to cause the display to display a histogram of the tracking value.

7. The medical apparatus according to claim 1, wherein the circuitry is further configured to cause an irradiation permission range to be displayed in a manner of being superimposed on the fluoroscopic image and change a color of the irradiation permission range when the target position of a position of a tracking target spot is settled within the irradiation permission range and an irradiation permission signal is output.

8. The medical apparatus according to claim 1, wherein the circuitry is further configured to cause an irradiation permission range to be displayed in a manner of being superimposed on the fluoroscopic image and change a hue or brightness of any of an inner region or an outer region of the irradiation permission range when an irradiation permission signal is output.

9. The medical apparatus according to claim 1, wherein the circuitry is further configured to issue a notification by a sound or a vibration when an irradiation permission signal is output.

10. The medical apparatus of claim 1, wherein the circuitry is further configured to determine the waveform of the tracking value without using a respiratory movement model relating a particular respiratory phase to a particular target position of the object.

11. The medical apparatus of claim 1, wherein the circuitry is further configured to
identify the target position in the time-series fluoroscopic images, and
determine the waveform of the irradiation permission signal indicating that the irradiation permission signal is output when the identified target position is settled within an irradiation permission range set in the time-series fluoroscopic images.

12. The medical apparatus of claim 1, wherein the circuitry is further configured to
target the target position identified in the time-series fluoroscopic images in each of a first direction indicating a body-axis direction of the object, a second direction indicating a front-rear direction of the object, and a third direction indicating a lateral direction of the object to determine three waveforms of the tracking value, and
cause the display to display the determined three waveforms of the tracking value.

13. A method executed by a medical apparatus, comprising;
acquiring information indicating a respiratory waveform of an object and acquiring fluoroscopic images of the object captured in time series;
determining a waveform of a tracking value of a coordinate position of a target position, the waveform of the tracking value being determined independently of the information indicating the respiratory waveform of the object, based directly on the time-series fluoroscopic images, the target position being an identified position of the object;
determining a waveform of an irradiation permission signal indicating whether the irradiation permission signal is output or not to a therapeutic device having a radiation source that irradiates the object with a therapeutic beam, the waveform of the irradiation permission being determined independently of the information indicating the respiratory waveform of the object, based directly on the time-series fluoroscopic images;
causing a display to display the respiratory waveform and the determined waveform of the tracking value of the coordinate position of the target position in a comparable form, the respiratory waveform and the determined waveform of the tracking value being displayed in a superimposed manner, and
causing the display to display, together with the respiratory waveform and the determined waveform of the tracking value, the waveform of the irradiation permission signal, wherein a time axis of the waveform of the irradiation permission signal is aligned with a time axis of the respiratory waveform and the determined waveform of the tracking value.

14. A medical apparatus, comprising:
circuitry configured to
acquire information indicating a respiratory waveform of an object and acquire fluoroscopic images of the object captured in time series,
determine a waveform of a tracking value of a coordinate position of a target position, the waveform of the tracking value being determined independently of the information indicating the respiratory waveform of the object, based directly on the time-series fluoroscopic images, the target position being an identified position of the object,
determine a waveform of an irradiation permission signal indicating whether the irradiation permission signal is output or not to a therapeutic device having a radiation source that irradiates the object with a therapeutic beam, the waveform of the irradiation permission being determined independently of the information indicating the respiratory waveform of the object, based directly on the time-series fluoroscopic images,
cause a display to display the respiratory waveform and the determined waveform of the tracking value of the coordinate position of the target position in a comparable form, the respiratory waveform and the determined waveform of the tracking value being displayed in a superimposed manner,
cause the display to display, together with the respiratory waveform and the determined waveform of the tracking value, the waveform of the irradiation permission signal, wherein a time axis of the waveform of the irradiation permission signal is aligned with a time axis of the respiratory waveform and the determined waveform of the tracking value, and
cause an irradiation permission range to be displayed in a manner of being superimposed on the fluoroscopic image.

15. A method executed by a medical apparatus, comprising;
acquiring information indicating a respiratory waveform of an object and acquiring fluoroscopic images of the object captured in time series;
determining a waveform of a tracking value of a coordinate position of a target position, the waveform of the tracking value being determined independently of the information indicating the respiratory waveform of the object, based directly on the time-series fluoroscopic images, the target position being an identified position of the object;
determining a waveform of an irradiation permission signal indicating whether the irradiation permission signal is output or not to a therapeutic device having a radiation source that irradiates the object with a therapeutic beam, the waveform of the irradiation permission being determined independently of the information indicating the respiratory waveform of the object, based directly on the time-series fluoroscopic images;
causing a display to display the respiratory waveform and the determined waveform of the tracking value of the coordinate position of the target position in a comparable form, the respiratory waveform and the determined waveform of the tracking value being displayed in a superimposed manner;
causing the display to display, together with the respiratory waveform and the determined waveform of the tracking value, the waveform of the irradiation permission signal, wherein a time axis of the waveform of the irradiation permission signal is aligned with a time axis of the respiratory waveform and the determined waveform of the tracking value; and causing an irradiation permission range to be displayed in a manner of being superimposed on the fluoroscopic image.

\* \* \* \* \*